(12) United States Patent
Sivovolenko

(10) Patent No.: US 7,259,839 B2
(45) Date of Patent: Aug. 21, 2007

(54) METHOD AND APPARATUS FOR EXAMINING A DIAMOND

(75) Inventor: Sergey B Sivovolenko, 129323 Sedova Street 13, Building 2, Room 216, Moscow (RU)

(73) Assignees: Garry Ian Holloway, Canterbury (AU); Sergey B. Sivovolenko, Moscow (RU)

( * ) Notice: Subject to any disclaimer, the term of this patent is extended or adjusted under 35 U.S.C. 154(b) by 339 days.

(21) Appl. No.: 10/861,063

(22) Filed: Jun. 4, 2004

(65) Prior Publication Data

US 2004/0246464 A1 Dec. 9, 2004

(30) Foreign Application Priority Data

Jun. 6, 2003 (AU) .............................. 2003902855

(51) Int. Cl.
*G01N 21/00* (2006.01)
*G01J 1/42* (2006.01)

(52) U.S. Cl. ......................................... 356/30; 250/372
(58) Field of Classification Search .................. 356/30; 359/803; 362/125
See application file for complete search history.

(56) References Cited

U.S. PATENT DOCUMENTS

| | | | | | |
|---|---|---|---|---|---|
| 1,700,496 | A | * | 1/1929 | Heitzler ......................... | 356/30 |
| 3,989,379 | A | * | 11/1976 | Eickhorst ....................... | 356/30 |
| 4,152,069 | A |   | 5/1979 | Bruck ........................... | 356/30 |
| 4,259,011 | A | * | 3/1981 | Crumm et al. ................. | 356/30 |
| 4,624,367 | A | * | 11/1986 | Shafer et al. ................ | 209/577 |
| 4,783,829 | A |   | 11/1988 | Miyakawa et al. ........... | 382/22 |
| 4,906,083 | A | * | 3/1990 | Sattler ......................... | 359/386 |
| 5,118,181 | A | * | 6/1992 | Yifrach et al. ................. | 356/30 |
| 5,184,732 | A |   | 2/1993 | Ditchburn et al. .......... | 209/576 |
| 5,424,830 | A | * | 6/1995 | Andrychuk .................... | 356/30 |
| 5,536,943 | A | * | 7/1996 | Smith et al. ................. | 250/372 |
| 5,544,254 | A |   | 8/1996 | Hartley et al. .............. | 382/108 |
| 5,811,817 | A | * | 9/1998 | Ravich ....................... | 250/372 |
| 6,020,954 | A | * | 2/2000 | Aggarwal ..................... | 356/30 |
| 6,239,867 | B1 |   | 5/2001 | Aggarwal ..................... | 356/30 |

(Continued)

FOREIGN PATENT DOCUMENTS

GB 1 416 568 10/1973

(Continued)

*Primary Examiner*—Gregory J. Toatley, Jr.
(74) *Attorney, Agent, or Firm*—Baker & Daniels LLP

(57) ABSTRACT

Prior methods of measuring diamond proportions in order to construct a complete model, such as a three dimensional virtual wire-frame model, of a diamond have been found to be inadequate. In particular, there has been no commercially available, automated and objective method for measuring the dimensions of a diamond with similar or greater accuracy as compared with the accuracy that can be achieved with manual gauges or micrometers. The present invention provides a method of measuring a physical characteristic of a facet of a diamond, such as the location of one or more points on an edge of a facet. The method comprises illuminating the diamond to visually distinguish a facet from adjacent facets when viewed from a predetermined location, and then capturing an image of the diamond as viewed from this predetermined location. The image is then analyzed to determine the location of at least one point located on an edge of a facet by identifying a discontinuity in the properties of light transmitted from the diamond to the viewing location.

30 Claims, 11 Drawing Sheets

U.S. PATENT DOCUMENTS

| | | | |
|---|---|---|---|
| 6,567,156 B1 * | 5/2003 | Kerner | 356/30 |
| 6,665,058 B1 * | 12/2003 | Gilbertson | 356/30 |
| 6,813,007 B2 * | 11/2004 | Lapa et al. | 356/30 |
| 6,980,283 B1 * | 12/2005 | Aggarwal | 356/30 |
| 2001/0023925 A1 * | 9/2001 | Smith | 250/372 |
| 2003/0071021 A1 * | 4/2003 | Benjano | 219/121.69 |
| 2005/0117145 A1 * | 6/2005 | Altman et al. | 356/30 |
| 2005/0213077 A1 * | 9/2005 | Sasian et al. | 356/30 |

FOREIGN PATENT DOCUMENTS

| | | |
|---|---|---|
| GB | 2 081 439 | 2/1982 |
| GB | 2 332 755 | 6/1999 |
| RU | 2 054 656 | 1/1993 |
| SU | 408200 | 12/1973 |
| WO | WO99/61890 | 12/1999 |
| WO | WO 02/099359 | 12/2002 |

* cited by examiner

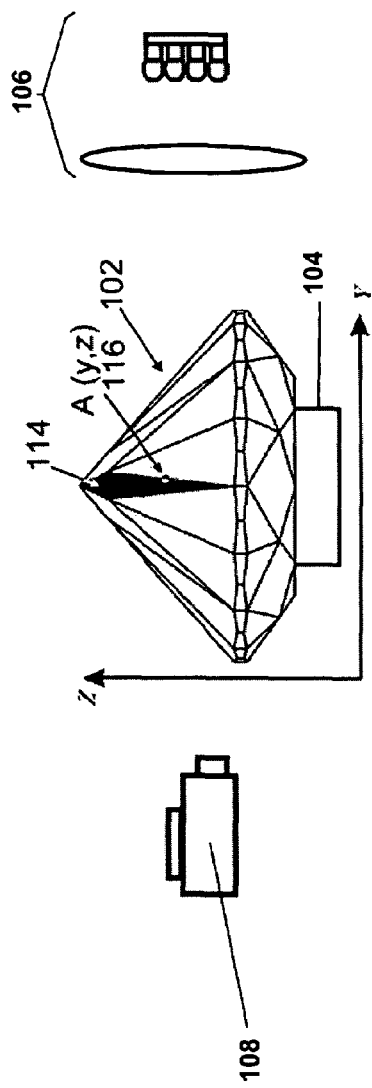
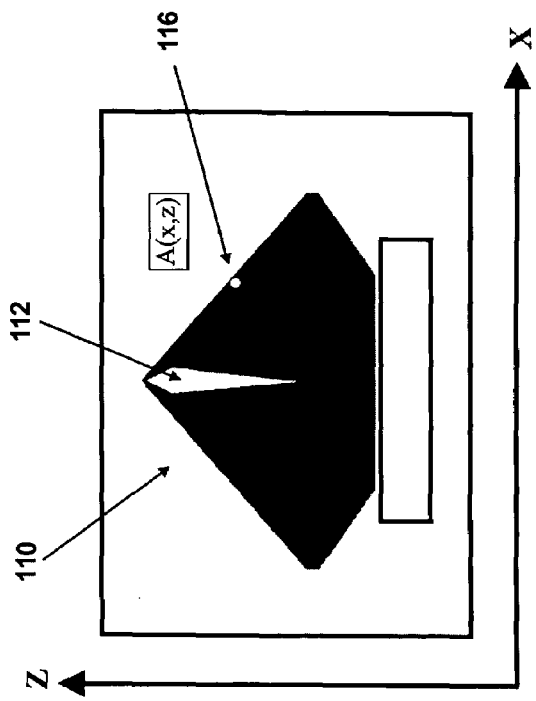
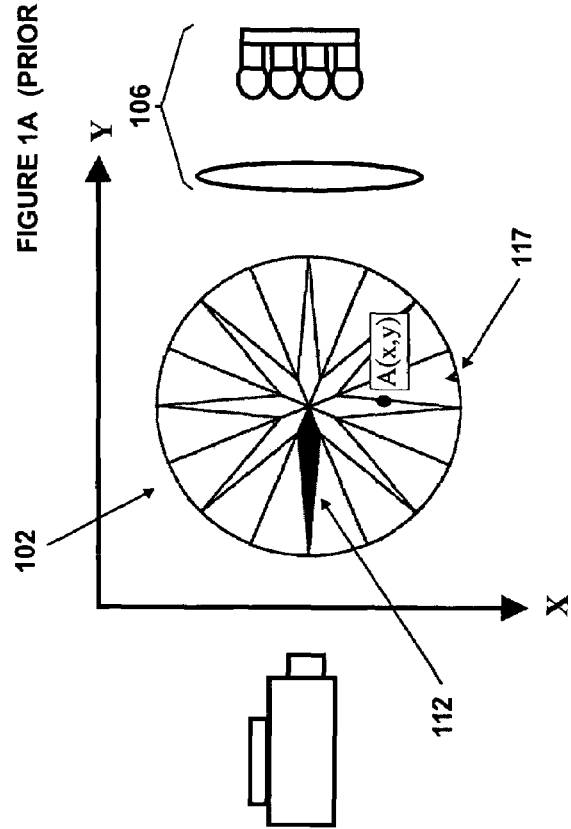
FIGURE 1A (PRIOR ART)
FIGURE 1B (PRIOR ART)
FIGURE 1C (PRIOR ART)

METHOD AND APPARATUS FOR EXAMINING A DIAMOND

FIELD OF THE INVENTION

The invention relates generally to a method and apparatus for examining a diamond, and in particular to a method and apparatus for accurately locating a facet of a cut diamond.

BACKGROUND OF THE INVENTION

The cut of a gem stone, such as a diamond, significantly affects its appearance and, in particular, the "brilliance" of the diamond. Features such as "brilliance" affect the commercial value of a diamond. Measures of the quality of a cut diamond include its proportions, symmetry and polish. Of these quality measures, only proportions have been routinely determined by automated means and graded, with acceptable accuracy, using calibrated apparatus in a repeatable and objective manner. Other measures, such as symmetry and polish, are still determined using manual methods, for example by an expert viewing the diamond through a microscope or other device for comparative symmetry grading purposes. Assessing these properties is thus a labour intensive task. Furthermore, these other quality measures therefore remain subjective and cannot be assessed in an objective manner that may be universally recognised.

In the past, attempts have been made to extend methods and apparatus designed for measuring diamond proportions in order to obtain additional information about the cut of the diamond. In principle, if sufficiently accurate measurements of the facet locations and dimensions can be obtained, a complete model, such as a three dimensional virtual wire-frame model, of the diamond can be constructed from which further properties, such as the symmetry of the diamond, can be determined. However, such attempts have proven inadequate. In particular, there has been no commercially available, automated and objective method for measuring the dimensions of a diamond with similar or greater accuracy as compared with the accuracy that can be achieved with manual gauges or micrometers. Furthermore, it has not been possible to measure facet angles to equivalent or greater accuracy than that with which the diamond can be cut using modern cutting tools and techniques. Thus there has been no objective method for distinguishing between diamonds of approximately the same quality of cut, even though an expert may be able to do so subjectively.

While there are computer aided methods being developed to rate the quality of cut of a diamond from a scanned wire frame model, the current accuracy of these methods is inadequate to provide a reliable indication of quality measures.

The most widely used apparatus and method for measuring the proportions of a cut diamond are illustrated in FIGS. 1A to 1C. For example, one commercial implementation of the method is that incorporated in the Sarin DiaMension proportion grading machine, although this is not the only such implementation. This prior art method is herein referred to as the "silhouette grading method".

In the silhouette grading method, a diamond 102 is seated upon a turntable 104 which may be actuated by, for example, a precision stepper motor mechanism to rotate the diamond about a central axis. The diamond is lit from behind by a light source and collimating lens arrangement 106 and viewed from the front by a camera and focussing lens arrangement 108. From the viewpoint of the camera, the diamond is seen in silhouette 110, with only the outline visible, the entire body of the diamond appearing dark. Thus, it is not possible to identify, in the images captured by the camera, any information regarding the location or dimensions of any of the facets of the diamond e.g. facet 112. It will therefore be understood that the contrasting shading of the facet 112 shown in FIGS. 1A to 1C is for illustrative purposes only, to assist in identifying the facet in the drawings, and does not represent any actual visible feature of the diamond 102.

The only facets of the diamond about which any information is directly available from the viewpoint of the camera are those comprising the edges of the silhouette image e.g. facet 114. Considering, for example, a point 116 labelled "A" in the drawing along an edge of the side facet 114, it is possible to identify in the silhouette image the X and Z coordinates of the point 116. However, no information regarding the Y coordinate is available.

Thus, it can be understood that, using the silhouette grading method, incomplete information is available regarding the precise locations in three dimensions of facet edges and vertices. The information available consists of that which can be observed in the outline of the stone as it is rotated. This information includes the diamond proportions such as table width, crown height, crown angle, girdle height, pavilion depth and pavilion angle. However, further information regarding the facet locations and dimensions in three dimensions must be calculated from this incomplete set of measured properties of the diamond. Although such calculation may be possible, subject to assumptions regarding the cut of the diamond, in practice the accuracy with which facet locations can be determined is highly dependent upon the accuracy of the original measurements.

For example, if a facet such as facet 114 shown in FIG. 1 is, in fact, slightly rotated towards or away from the plane perpendicular to the camera, it will be appreciated that the measured angle of the facet will be subject to an error that will prevent the construction of an accurate wire-frame model.

In this regard, small errors in measurements of angles may result in a wire frame model of the diamond in which facet edges apparently do not meet correctly in a single vertex even when the measured diamond is almost perfect, and all edges in fact meet at the vertex. This problem is illustrated in FIG. 2, which shows a top view of a wire-frame model of a diamond obtained from the silhouette grading method. Whereas the real diamond may be perfectly cut, the model includes facet junctions that are not accurately determined. For example, the distinct junctions 202, 204 should in fact meet at a single point. Additionally, the distinct junctions 206, 208 should also meet at a single point, symmetrically placed with respect to the actual common meeting point of junctions 202, 204. Such errors make it impossible to assess the symmetry of the diamond by automated analysis of a model. While it is possible to employ computer algorithms to "close" the facet junctions on the wire-frame model, this method has the drawback that it is impossible to completely distinguish between measurement errors and actual instances of diamonds with poor facet meeting. Accordingly, such algorithms may result in a wire-frame model that has better symmetry than the original diamond.

As a result, it therefore remains necessary to employ the services of an expert human operator to examine every facet junction with the aid of a microscope. Improved accuracy of current wire frame modelling is also required for practical implementation of computerised methods for grading of cut quality.

FIG. 3 illustrates an apparatus that allows the silhouette grading method to be extended into a third dimension. In this apparatus, an additional camera and lens arrangement 302 is located above the diamond 102 in order to capture a top view of the stone. However, from the viewpoint of the additional camera 302, the diamond 102 is still seen only in silhouette, and there is therefore no further information available regarding the Y coordinate of the point "A" 116 which, when viewed from the top, is located within the dark silhouette image. This extended arrangement overcomes one problem of the single camera apparatus, in that it is now possible to identify indentations 117 in the girdle of the diamond 102 which are not visible from the viewpoint of the first camera. However, the arrangement offers no further benefit in obtaining the correct dimensions and locations of the facets of the diamond.

A further extension of the silhouette grading method, disclosed in U.S. Pat. No. 6,567,156, involves the use of a coherent collimated beam of laser light, directed towards a diamond at an angle of approximately 30 degrees to the horizontal. The image of an oblique laser beam as observed on the diamond facets is captured by the camera 108. The purpose of this extension to the method is to identify indentations in the stone, and especially in uncut and partly cut stones, that cannot be detected from the camera positions 108, and that are not always in view of the camera 302 in the previously described methods. However the method is, in fact, less accurate than the standard silhouette grading method in determining the proportions of the diamond, and is therefore less suited for accurately determining the locations of the facets.

It is therefore an object of the present invention to mitigate at least one of the abovementioned problems in the prior art, and in particular to provide an apparatus and method by which the location and dimensions of a facet of a diamond may be more accurately determined.

Any discussion of documents, devices, acts or knowledge in this specification is included to explain the context of the invention. It should not be taken as an admission that any of the material formed part of the prior art base or the common general knowledge in the relevant art on or before the priority date of the claims herein.

SUMMARY OF THE INVENTION

In one aspect, the present invention provides a method of measuring a physical characteristic of a facet of a diamond comprising the steps of:

illuminating the diamond to visually distinguish said facet from adjacent facets when viewed from a predetermined location;

capturing an image of the diamond as viewed from said predetermined location; and analysing said image to determine of the location of at least one point located on an edge of said facet by identifying a discontinuity in the properties of light transmitted from the diamond to the viewing location.

According, whereas known methods enable facets to be used only in profile, whereby it is impossible to accurately determine the distance of points on the edges of the facets from the viewing location, the method of the present invention enables facets to be illuminated and viewed from other angles in order to determine the corresponding unknown coordinates of such points.

It is particularly preferred that said predetermined location is substantially positioned in a plane oriented perpendicular to a surface of said facet, and that the direction of viewing from said predetermined location towards the diamond along a line substantially normal to an access thereof. In such a preferred arrangement, a facet may be illuminated and viewed substantially face on, so that unknown coordinates may be determined with the greatest accuracy.

The step of illuminating preferably comprises illuminating the diamond using a controlled lighting source. The controlled lighting source may comprise an array of discrete light emitters, and the step of illuminating the diamond may include activating or deactivating one or more emitters of the array.

In some embodiments, the step of illuminating may include illuminating the diamond using a source of light having a plurality of colours and/or shades. In particular, the step of illuminating may comprise illuminating a screen having a plurality of bands of varying or discontinuous colour or shade, said screen been placed substantially behind the diamond relative to the viewing location, such that said facet is visually distinguished by means of discontinuities in colour or shade of light emitted from a surface of said facet after being transmitted from said screen through the diamond. Such an arrangement has the benefit of simplicity, since it may be possible to avoid the need for a controlled lighting source.

Preferably, the step of illuminating comprises illuminating the diamond using one or more light emitters located relative to the viewing location such that the facet is visually distinguished by light reflected from the facet. Alternatively or additionally, the step of illuminating may comprise illuminating the diamond using one or more light emitters located relative to the viewing location such that the facet is visually distinguished by light transmitted through the diamond and emitted from said facet.

According to preferred arrangements, mirrors and/or additional light emitters may be located below the diamond to illuminate lower facets. Accordingly, through the use of combinations of such arrangements, it is possible to ensure that any facet of a diamond may be illuminated, regardless of the shape or cut of the diamond.

The step of capturing an image preferably includes capturing a digital image, and the step of analysing preferably includes analysing the digital image using a computer.

The discontinuity may be between adjacent brighter and darker regions of said image. Specifically, a brighter region may result from a light generated by a source of illumination that is reflected from a surface of said facet towards the viewing location. Alternatively, a brighter region may result from light generated by a source of illumination and transmitted through the diamond and emitted from a surface of said facet.

In some embodiment of the invention, the discontinuity may be between adjacent regions of differing colour or shade resulting from light generated by source having a plurality of colours or shades, said light being transmitted through the diamond and emitted from respective surfaces of said adjacent facets.

The step of analysing preferably includes determining an unknown coordinate of the at least one point located on an edge of a facet by identifying a point on the edge corresponding to at least one known coordinate of said point. According to an alternative method of analyses, the step of analysing includes determining at least one unknown coordinate by identifying a point on a line corresponding to at least one known coordinate of said point at which there is a discontinuity in the properties of the light transmitted from the diamond to the viewing location.

In another aspect, the invention provides an apparatus for measuring a physical characteristic of a facet of a diamond by illuminating the diamond, capturing an image of the diamond, and analysing the image, the apparatus comprising:

a support for the diamond within the apparatus;

at least one camera positionable at a predetermined location for capturing an image of the diamond;

a light source for illuminating the diamond to visually distinguish said facet from adjacent facets when viewed from the location of the camera; and a processor for analysing said image to determine the location of at least one point located on an edge of said facet by identifying a discontinuity in the properties of light transmitted from the diamond to the viewing location.

The camera may be located at a fixed position relative to the support, and the support may be operable to orient the diamond relative to the camera. In a particularly preferred embodiment, the support comprises a turntable operable to rotate the diamond. Of course, it will be appreciated that other arrangements are possible. For example, the camera may be moveable relative to the support, and/or multiple cameras may be arranged to provide different viewing locations.

In a further aspect, the invention provides a method of obtaining data for the construction of a three dimensional model of a diamond comprising the steps of:

illuminating the diamond to visually distinguish each facet of said diamond from adjacent facets;

capturing images of each of the visually distinguished facets of the diamond; and analysing said images to determine the location of a plurality of points located on the edges of said facets thus enabling determination of the locations of the edges of all of said facets of the diamond.

The method may further comprise the step of constructing an initial approximate model of the diamond whereby the step of analysing comprises determining a plurality of points located on the edges of said facets thus enabling determination of the locations of the edges of all of said facets of the diamond and using this additional information to refine said approximate model. In a particularly preferred embodiment, the step of constructing an initial approximate model comprises constructing a model of the diamond using a silhouette grading method.

Accordingly preferred embodiments of the invention provide a method of constructing a three dimensional model of a diamond comprising the steps of:

constructing an initial approximate model of the diamond using a silhouette grading method;

illuminating the diamond to visually distinguish each facet of said diamond from adjacent facets;

capturing images of each of the visually distinguished facets of the diamond; and analysing said images to determine a plurality of points located on the edges of said facets thus enabling determination of the locations of the edges of all of said facets of the diamond and using this additional information to refine said approximate model.

BRIEF DESCRIPTION OF THE DRAWINGS

Preferred embodiments of the present invention will now be described, without limitation upon the overall scope of the invention, with reference to the accompanying drawings in which:

FIGS. 1A to 1C are diagrams illustrating a prior art apparatus and method for measuring the proportions of a diamond;

DESCRIPTION OF PREFERRED EMBODIMENTS

Figure 2:
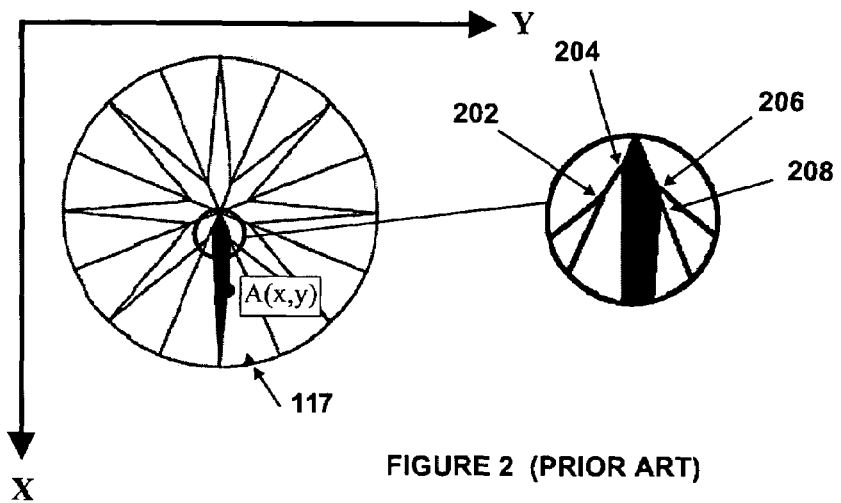
FIG. 2 is a diagram illustrating an exemplary facet location estimation error inherent in a prior art measurement method.
Figure 3:
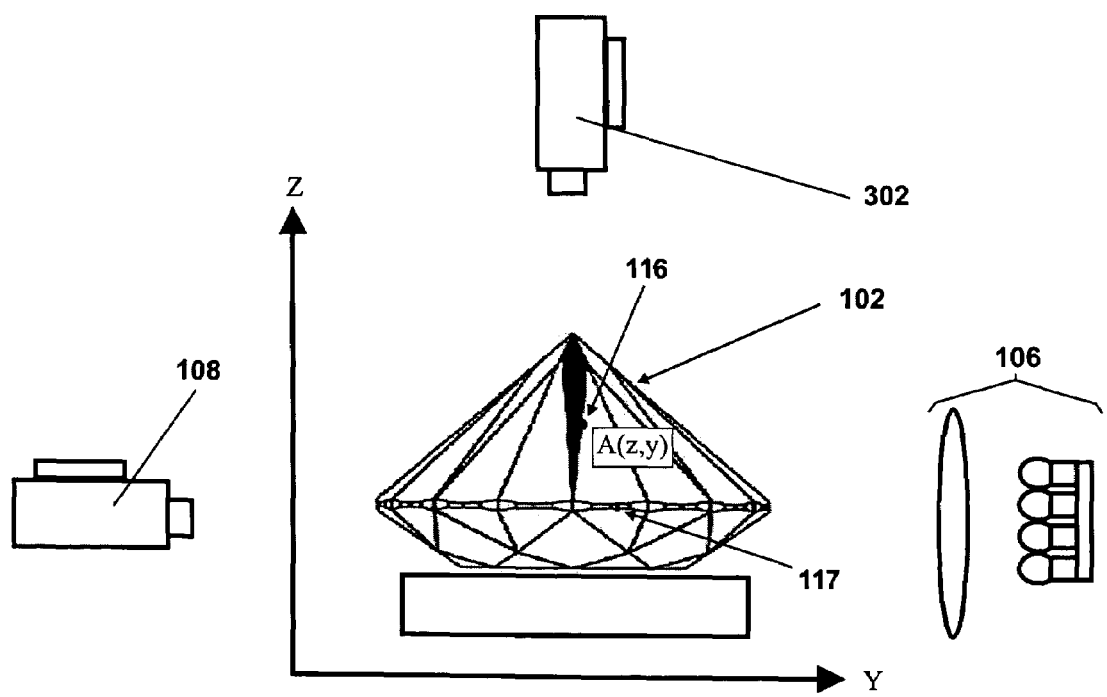
FIG. 3 is a diagram illustrating a further prior art apparatus for detecting indentations in a girdle edge of a diamond.
Figure 4:
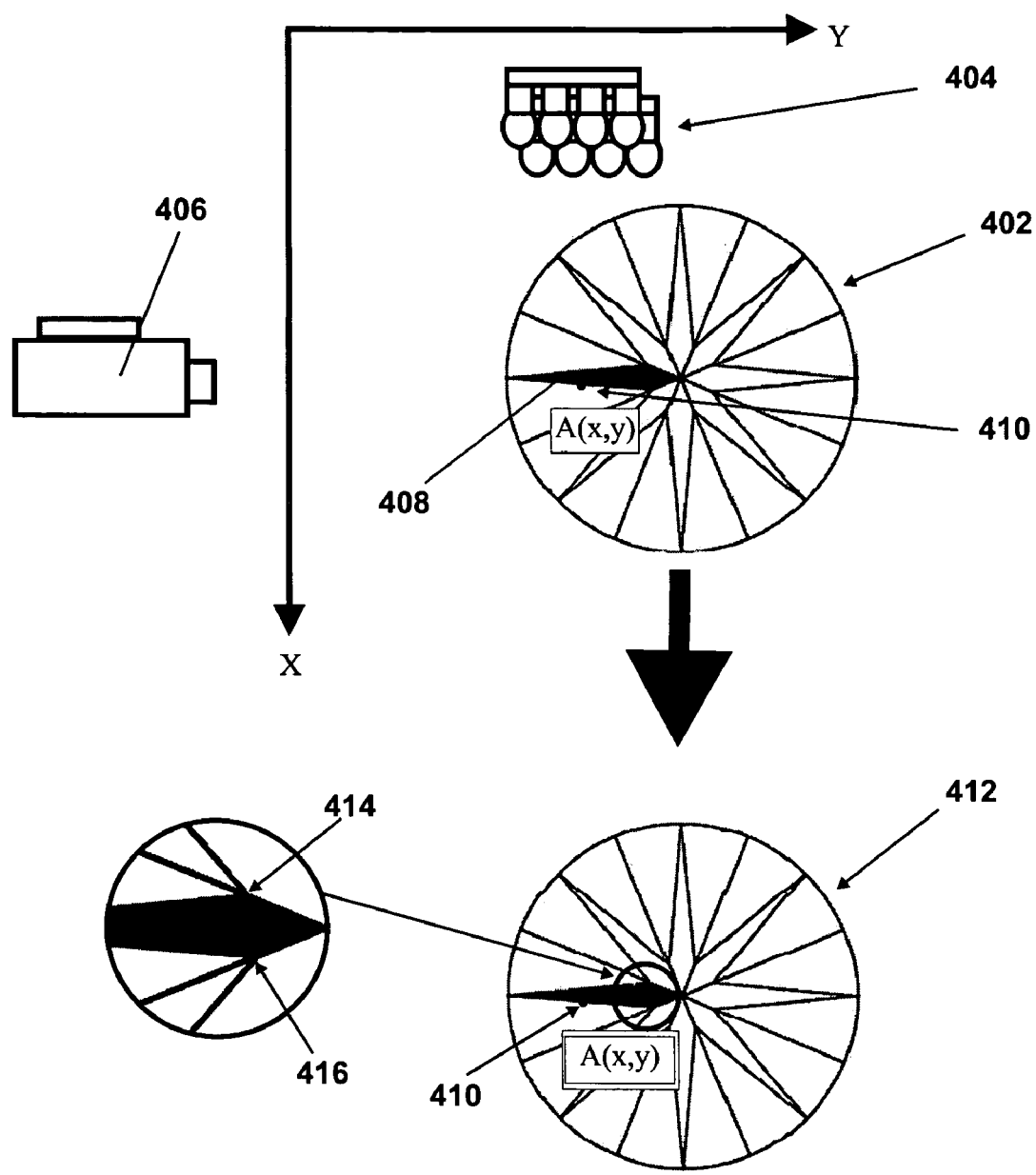
FIG. 4 is a diagram illustrating a method of locating a pavilion facet of a diamond according to the present invention.

FIG. 4 shows schematically a top view of an apparatus for locating a facet 408 of a diamond 402. In the arrangement shown, the diamond 402 is placed on a turntable (not visible in the figure) resting upon its table such that the pavilion of the diamond is facing upwards. The facet 408 identified in FIG. 4 is consequently a pavilion facet.

A light source 404 is provided in the preferred arrangement to illuminate the diamond. In the preferred embodiment, the light source 404 includes an array of light emitters arranged such that each individual emitter may be activated and deactivated independently of the others. For example, the emitters 404 may be light emitting diodes that can be controlled by a computer (not shown). Although eight light emitters are shown in FIG. 4, envisaged as being located above the diamond and emitting light generally downwards, this is for illustrative purposes only. It will be appreciated that the light sources 404 are shown schematically, and that their positioning in FIG. 4 is not intended to represent the actual location of the emitters in a practical assembly. In an actual embodiment there may be a greater or lesser number of emitters arranged around the diamond as required. For example, an array of emitters 404 may be distributed in a hemispherical or dome arrangement over and around the diamond 402.

An image capture device 406 is arranged at a viewing point in front of the diamond 402, and directed towards the diamond 402. In the preferred embodiment, the image capture device 406 includes a digital camera and a lens arrangement to focus light from the diamond 402 efficiently onto the camera. The facet 408, which is to be located, is rotated such that it faces towards the camera 406. This means that according to this arrangement, the facet 408 of interest is rotated by approximately 90 degrees with respect to its location for viewing by the silhouette grading method, which is only able to view the facet in profile. A significant advantage of the arrangement is that it is able to view the facet 408 face-on in order to more accurately determine its location and dimensions.

It is preferred that the emitters in the lighting array 404 may be activated in a selective manner, such that the facet 408 preferentially reflects light from the active emitters towards the camera 406. Thus the facet 408 will be clearly visible as a bright region in an image captured by the camera. The rotation of the diamond 402, and the combination of active emitters can be adjusted, for example under computer control, to identify a satisfactory rotation and lighting arrangement for viewing the facet 408.

It is advantageous to provide for control of the lighting source in this manner, to enable a facet, e.g. 408, to be clearly illuminated regardless of its angle and orientation with respect to the camera 406. However, a fixed, uncontrolled lighting source could also be used, with the limitation that it may be less effective in illuminating some diamond facets. An arrangement having a fixed lighting source may therefore be limited in its application to diamonds having specific cuts within a defined range of facet angles.

The image captured by the digital camera 406 is analysed to determine the location and dimensions of the facet 408. In the preferred embodiment, the image is transferred to a computer, and an analysis is performed using a computer program. The analysis may consist of processing the digital image to identify edges at which there are discontinuities in the image, such as between the brightly-lit facet 408, and the surrounding facets of the diamond. Methods for performing such analyses are known in the art of digital image processing and, for example, functions that convert images into line drawings using these methods are available in image editing programs.

The result of the analysis is a model of the facet 408 that includes the locations of the edges and junctions of the facet 408 as viewed from the position of the camera 406. Furthermore, the azimuth of the facet 408 is known from the degree of rotation of the diamond that was set at the time the image was captured. In addition, the angle of the facet 408, being in this example the pavilion angle, may be determined with greater accuracy using the silhouette grading method after rotating the diamond 402 through 90 degrees to view the facet in profile, and illuminating the diamond 402 substantially from the rear because it is now possible to more accurately orient the pavilion facet 408 perpendicular to the direction of view of the camera 406. Rear illumination of a diamond may be achieved using a dedicated rear light source (not shown), such as is used in the silhouette grading method, or it may be achieved by appropriate activation of the controlled light source 404.

As will be appreciated from the foregoing description, similar results may be achieved using alternative arrangements that would be apparent to those skilled in the art. For example, instead of using a controlled array of light emitters, moveable lighting source could be employed. Furthermore, instead of rotating the diamond, the camera could be rotated about the diamond, or multiple cameras could be provided. By combining these variations, many possible arrangements are possible that may be considered to be functionally equivalent.

To be more specific, the object of the analysis may be reduced to that of determining the location of any point A, e.g 410, on a specified facet edge with greater accuracy than can be achieved using prior art methods. The X and Z coordinates of the point may be determined from the silhouette of the diamond, as, for example, in the known arrangement illustrated in FIG. 1. However, the silhouette image provides no accurate information about the distance of the point A 410 from the camera 406.

To obtain a more accurate determination of the Y coordinate of the point A 410, which in prior art methods is determined by implication, the diamond is rotated relative to the camera, for example through 90°, and the facet 408 then illuminated in accordance with the invention. A clear image of the facet 408 can then be captured, enabling the transverse (X) coordinate of the rotated point, corresponding to the unknown Y coordinate of the point prior to rotation, to be accurately determined.

While it is preferred that the rotation of the diamond be through 90°, it will be appreciated that other angles of rotation may also enable the facet 408 to be illuminated from the position of the camera so that the transverse coordinate of the rotated point may be determined. For example, if the diamond is instead rotated through 45°, it will be visible from the viewing location, although it will appear to be compressed in width by a factor equal to the square root of two, due to the effect of perspective. This known scaling effect can be taken into account when calculating the location of the point A 410, however there is a corresponding reduction in precision of the measurement, since the captured image is, in practice, of finite resolution.

In this regard, it will also be appreciated that "accuracy" is a relative term, and the actual accuracy which the location of a point, e.g. A 410, can be determined is dependent upon the precision and resolution of the measuring apparatus. Accordingly, it will be understood that when reference is made in this specification to the goal of accurately determining or defining the location of a feature of a diamond, it is intended to refer to the object of locating the feature with greater accuracy than is possible using prior art methods.

By determining the locations of any two or more such points on any edge in this manner, the line in three dimensional space corresponding to the edge may be accurately defined.

While the foregoing description relates to the determination of the unknown coordinate Y following determination of the X coordinate using the silhouette method, it will be appreciated that the present method may be used to determine an unknown transverse coordinate of a point located on a facet edge independently of the silhouette grading method. For example, by choosing any desired value of the Z coordinate, the corresponding transverse coordinate of an edge of a facet illuminated according to the invention may be determined.

In general, given one known (e.g. Z) coordinate of a point on a facet edge, the method enables a corresponding unknown (e.g. X) coordinate to be determined. The unknown coordinate may be identified as the corresponding coordinate of the point on the edge having the known coordinate. This point is equivalently a point having the known coordinate at which a discontinuity is identified in the captured image.

Having identified the edges and junctions of the facet 408, its angle and its azimuth, the location of the facet 408 on the diamond is fully determined. By repeating this process for each facet on the pavilion of the diamond, a complete model 412 of the pavilion facets is established. The additional information regarding the edge and junction locations of each facet, e.g. 408, obtained using the method of the invention enables a more accurate determination of the facet locations of the diamond as compared with prior art methods, at least to tolerances presently required by diamond grading laboratories. Accordingly, errors in determining the edge and junction locations are significantly, and facet junctions at which a number of facet edges meet, e.g. 414, 416, are more accurately identified. Additionally, a method according to the present invention enables the location of any point on an edge, such as the point "A" (410), to be determined in all three dimensions.

A similar procedure may be followed in order to determine the locations and dimensions of facets on the crown of the diamond. However, since the crown facets are located under the diamond, and are occluded by the pavilion and girdle when viewed from above, it is preferred to arrange for the diamond to be lit from below. One arrangement that achieves this objective is to locate light emitters of the controlled lighting source below the height of the girdle of the diamond. This is a simple solution, however it clearly requires additional light emitters for measurement of the crown facets.

Figure 5:
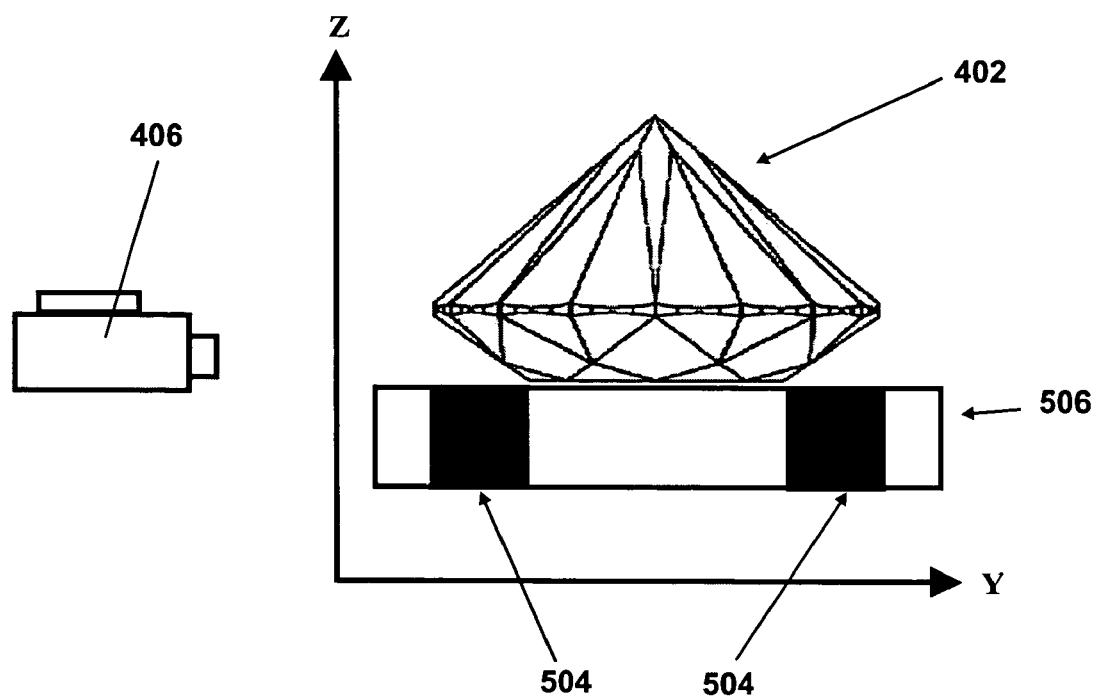
FIG. 5 illustrates a method for locating a crown facet of a diamond according to the present invention.

One particular embodiment in which light emitters are located below the girdle of the diamond is shown in FIG. 5. The diamond 402 rests on turntable 506, and is viewed from the front by camera 406, and illuminated from below by light emitters 504 built into turntable 506. Accordingly, light emitters 504 may be activated to illuminate crown facet, e.g. 502, such that light reflected from facet 503 is directed towards camera 406 to produce a clear image of the facet 502.

Figure 6:
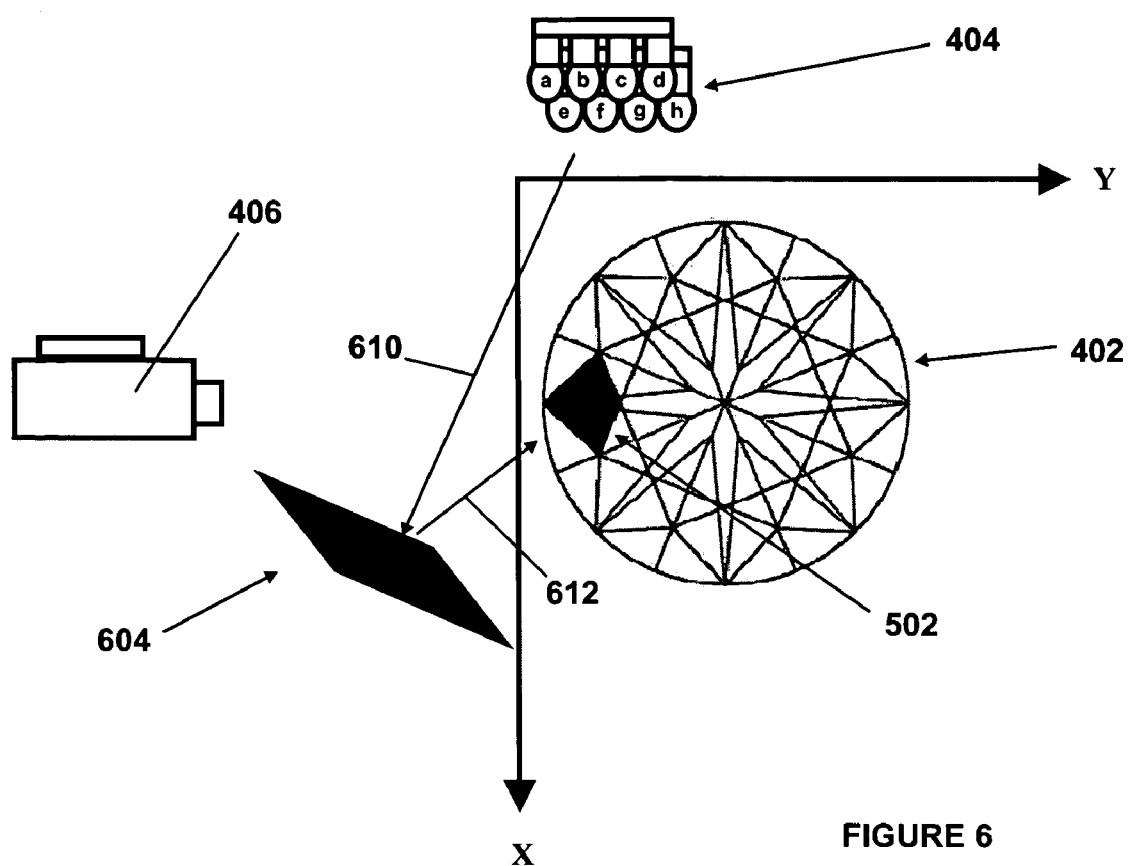
FIG. 6 illustrates an alternative arrangement for locating a crown facet of a diamond according to the present invention.

An alternative arrangement for lighting the crown facets is illustrated in FIG. 6, wherein the diamond 402 is again viewed from the top. An array of emitters 404 is located above the diamond 402, and a camera 406 is located in front of the diamond 402. A crown facet 502 is to be located. Rather than placing additional emitters below the girdle of the diamond 402, a mirror 604 is located below the diamond 402.

By activating emitters in the lighting array 404 in a selective manner, light 610 reflected from the mirror 604 is directed 612 towards the crown facet 502 which will preferentially reflect this light towards the camera 406. Thus the crown facet 502 will now be clearly visible as a bright region in an image captured by the camera. As with the measurement of the pavilion facets, the rotation of the diamond 402, and the combination of active emitters can be adjusted, for example under computer control, to identify a satisfactory rotation and lighting arrangement for viewing the crown facet 502.

Although a specific arrangement of the mirror 504 is illustrated in FIG. 6, the mirror arrangement may be straightforward. For example, by placing the entire arrangement including the turntable supporting the diamond 402 and the light emitters 404 above a horizontal mirrored surface, each light emitter located above the diamond is effectively complemented by a corresponding virtual light emitter located as a mirror image below the diamond 402. A limitation of this straightforward arrangement, however, is that if the crown facet angle is less than 45°, light from the virtual light emitters will not be reflected from the crown facet in the direction of the camera 406, and thus from the position of the camera 406 the crown facet will never be clearly illuminated.

Figure 7:
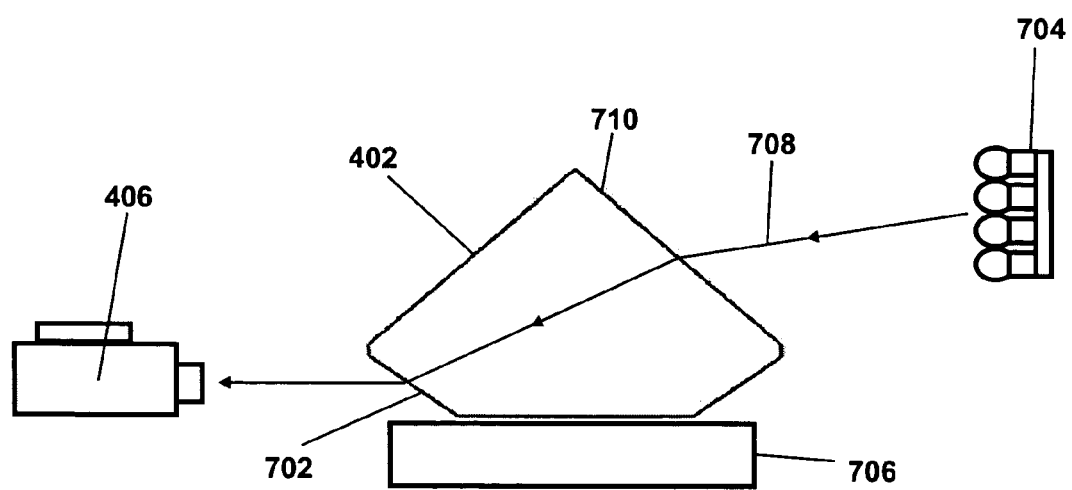
FIG. 7 illustrates another alternative arrangement for locating a crown facet of a diamond according to the present invention.

Yet another possible arrangement for illuminating the crown facets is illustrated in FIG. 7. Once again, the diamond 402 rests on a turntable 706, and a camera 406 is located in front of the diamond 402. A crown facet 702 is to be located. An array of light emitters 704 is located above the girdle of the diamond 402, and behind the diamond 402 relative to the camera 406.

With the diamond 402 rotated on the turntable 706 such that the crown facet 702 faces towards the camera 406, at least one of the light emitters 704 may be activated. By activating the appropriate light emitter, corresponding light rays, e.g. 708, enter the diamond through a pavilion facet 710 located opposite the crown facet 702. The ray is reflected at the facet 710 and passes through the diamond 402 to strike the interior of the crown facet 702. The ray is refracted again at the crown facet 702 such that it exits the facet in the direction of the camera 406. Accordingly, activation of light emitters 704 may result in illumination of the desired crown facet 702 by transmission of emitted light through the diamond 402.

The arrangement shown in FIG. 7 is most effective when it is known in advance which of the emitters 704 should be activated in order to illuminate the crown facet 702 through the processes of internal refraction of light rays 708. It is possible to predict the path of ray 708 using standard ray tracing techniques if estimates of the angles of the facets 702 and 710 are available. Such estimates can be obtained, for example, by using the standard silhouette grading method. However, it is preferred that the angle of the facet 710 be known to relatively high accuracy, since any error in this angle results in a larger error in the predicted angle at which the ray 708 emerges from the crown facet 702. Accordingly, it is preferred that if the technique depicted in FIG. 7 is to be used for illuminating the crown facets, an accurate model of the pavilion facets is first constructed using methods in accordance with the invention such as those described following with reference to FIGS. 8 and 9.

While a facet of a diamond can be located by the above described procedures by any suitable method of searching for the preferable rotation and lighting arrangement, including an exhaustive trial and error approach, the time required to construct a complete wire-frame model of a diamond may be significantly reduced if it is possible to identify suitable measurement settings more directly. Accordingly, in at least preferred embodiments, the present invention provides an improved method of constructing a three dimensional wire-frame model of a diamond.

According to the preferred method, an approximate model of the diamond is first constructed. This model of the diamond does not need to be highly accurate, and in particular it is only necessary to determine the number and approximate locations of the flat faces of the facets. Errors in the location of the edges and junctions are not consequential. Thus a suitable model may be obtained using an approximate measurement method to estimate the locations of the facets. In particular, the silhouette grading method is suitable for this purpose. The approximate model is then analysed in order to determine suitable rotations and controlled lighting arrangements for highlighting the facets to be measured.

Figure 8:
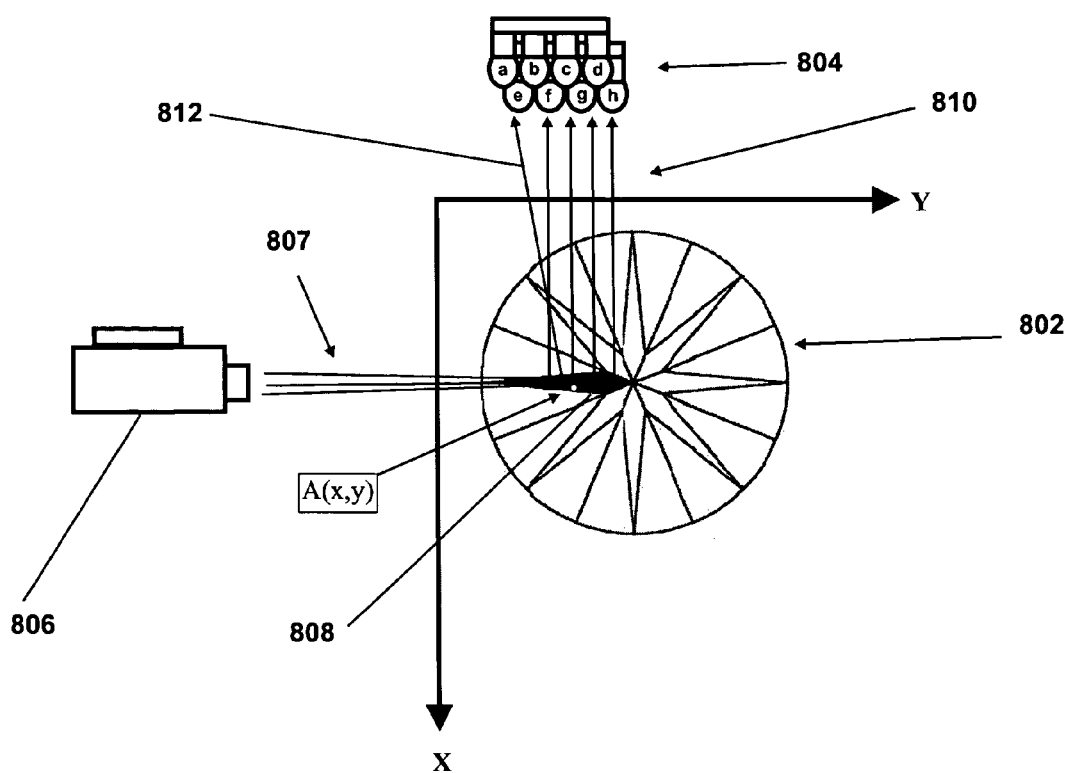
FIG. 8 is a diagram illustrating a method of reverse ray tracing according to the present invention.

One method of analysis of an approximate model according to the invention is illustrated in FIG. 8. The analysis employs the approximate model of the diamond 802. The locations of the controlled lighting source 804 and camera, around the diamond 802, are also included in the analysis. The analysis is based on a method of reverse ray tracing. Ray tracing normally involves calculating the paths of critical light rays from light sources to a desired viewing position in a three dimensional virtual space in order to generate an image representing the view of the space as seen from the viewing position. The method employed in the preferred embodiment of the invention reverses this analysis in order to determine the lighting arrangement required to obtain a desired image at the viewing point, in which a selected facet of the diamond is preferentially lit as required.

According to the reverse ray tracing method, the paths of light rays 807 are traced back from the location of the camera 806 onto the face of the desired facet 808 of the diamond model 802. The reversed reflections of the rays, e.g. 810, are then traced back to the respective locations of the light sources in the array 804 from which they would be emitted. In the process, it will also be found that certain paths, such that indicated by the crossed ray 812, do not exist, and thus that light emitted from the corresponding emitters will not reach the camera 806 via direct reflection from the facet 808.

Accordingly, the reverse ray tracing method identifies those emitters, e.g. 804*f*, 804*g*, 804*h*, from which light will be reflected from the facet 808 onto the camera 806, and those emitters, e.g. 804*e*, from which light will not reach the camera 806 via direct reflection from the facet 808. Consequently, it is beneficial to activate the corresponding actual emitters 404*f*, 404*g*, 404*h* when performing the measurement of the location and dimensions of the facet 408 of the real diamond, in order to highlight the facet 408. However, it is not beneficial to activate the unselected emitters because they will not contribute to light received from the facet 408 by the camera 406. Indeed, it may be detrimental since light from these emitters may in fact reach the camera 406 via reflection from other facets including adjacent facets to the desired facet 408, thus reducing the contrast between the facet 408 and other facets.

FIGS. 9A to 9D illustrate a method for improving the accuracy of the three dimensional wire-frame model by illuminating facets by a method according to an embodiment of the present invention. Once an approximate wire-frame model of the diamond has been constructed, the diamond 900 may be rotated to a desired position and a facet 902 of the diamond 900 illuminated as shown for example in FIG. 9A. The figure shows an example of a crown facet 902 illuminated by light rays transmitted through the diamond, in accordance with an embodiment of the invention as depicted in FIG. 7, however it will be appreciated that any desired facet may be illuminated in accordance with any appropriate lighting arrangement such as any one of the arrangements described herein.

Figure 9A:
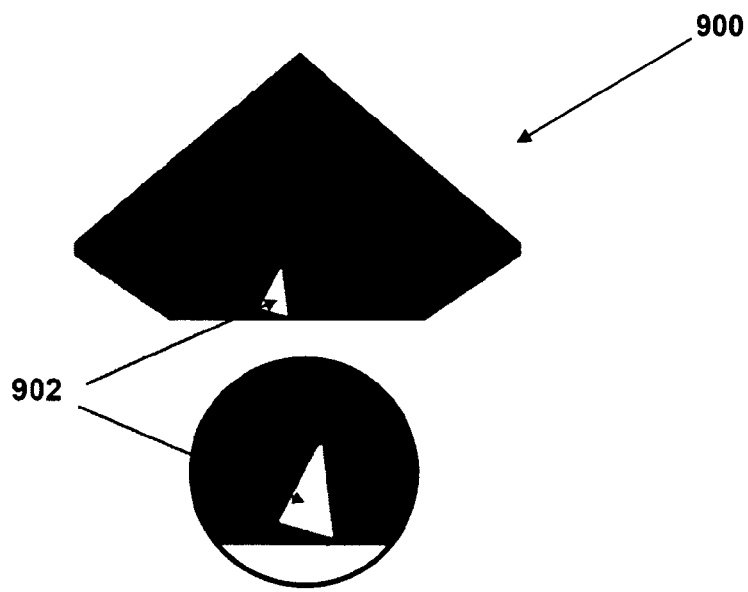
FIGS. 9A to 9D illustrate a preferred method of improving the accuracy of a model of a diamond.
Figure 9B:
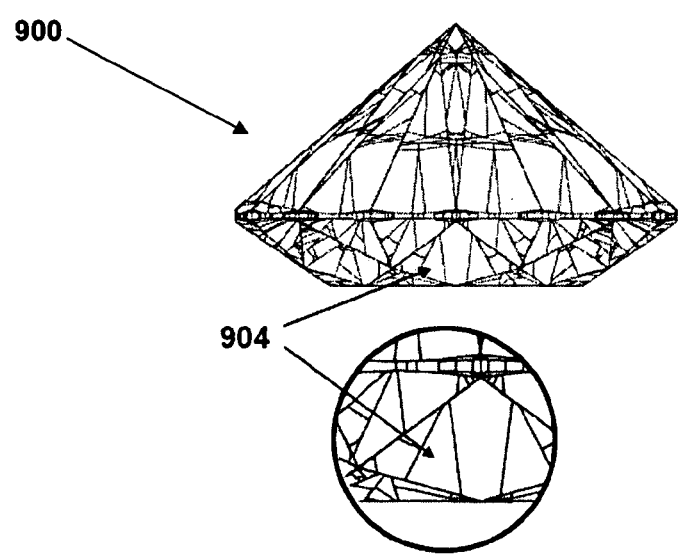

FIG. 9B illustrates an approximate virtual wire-frame model of a diamond constructed, for example, from initial measurements conducted according to the silhouette method. This wire-frame model is shown with secondary internal reflections predicted using ray tracing software. Accordingly, the wire-frame includes not only the outlines of the exterior facets, but also the "virtual facets", e.g. 904, that result from internal reflections and refraction of light.

Figure 9C:
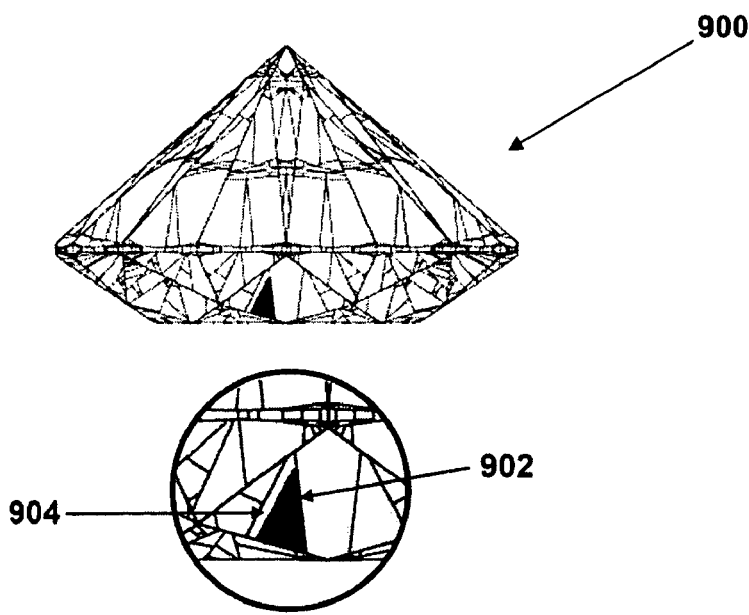

FIG. 9C shows the illuminated facet segment 902 of FIG. 9A superimposed upon the corresponding segment 904 of the wire-frame model shown in FIG. 9B. It is apparent that the actual observed facet segment is not an exact match with the segment predicted from the wire-frame model. However, it is possible by rotating the azimuth of the facet clockwise to align the predicted wire-frame position with the actual illuminated region. This enables the approximate wire-frame mode to be refined to more precisely correspond with the actual diamond.

After performing the procedure on only a single facet or single facet segment the wire-frame model may not yet provide an improved approximation to the actual diamond because the adjoining facets have not been similarly refined. In order to produce an overall improvement in accuracy, in one embodiment of the invention all pavilion and crown facets may be adjusted in a first pass around the model, and a further complete rotation and realignment may then be performed to result in a further improved wire-frame model.

In an alternative embodiment of the method, images may be captured of successive adjacent illuminated facets or facet segments, and the common edges between the adjacent facets realigned to produce a refined wire frame model in which an improved match is obtained for both of the adjacent facets. In this manner, a sufficiently accurate wire-frame model may be produced in a single pass around the diamond.

Figure 9D:
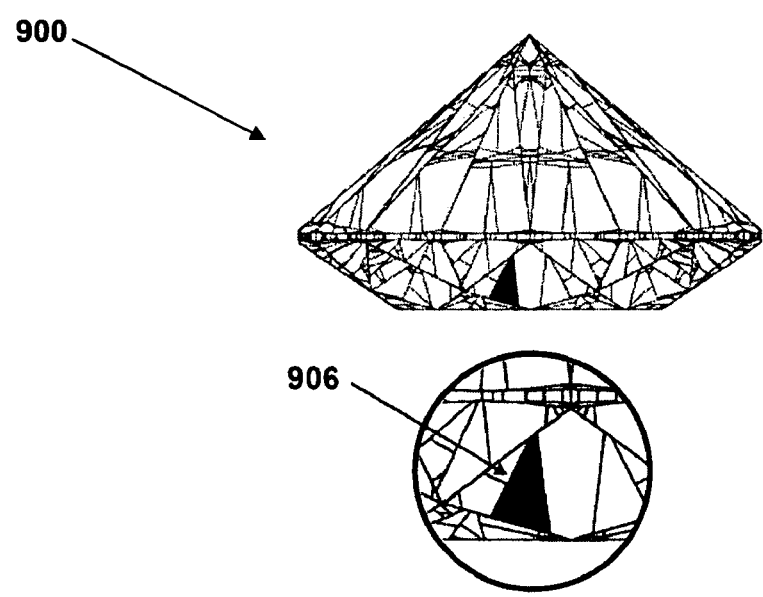

The result of the realignment process is depicted in FIG. 9D, in which a refined wire-frame crown facet segment 906 is shown where the edges are now correctly aligned with the actual illuminated facet segment.

Figure 10A:
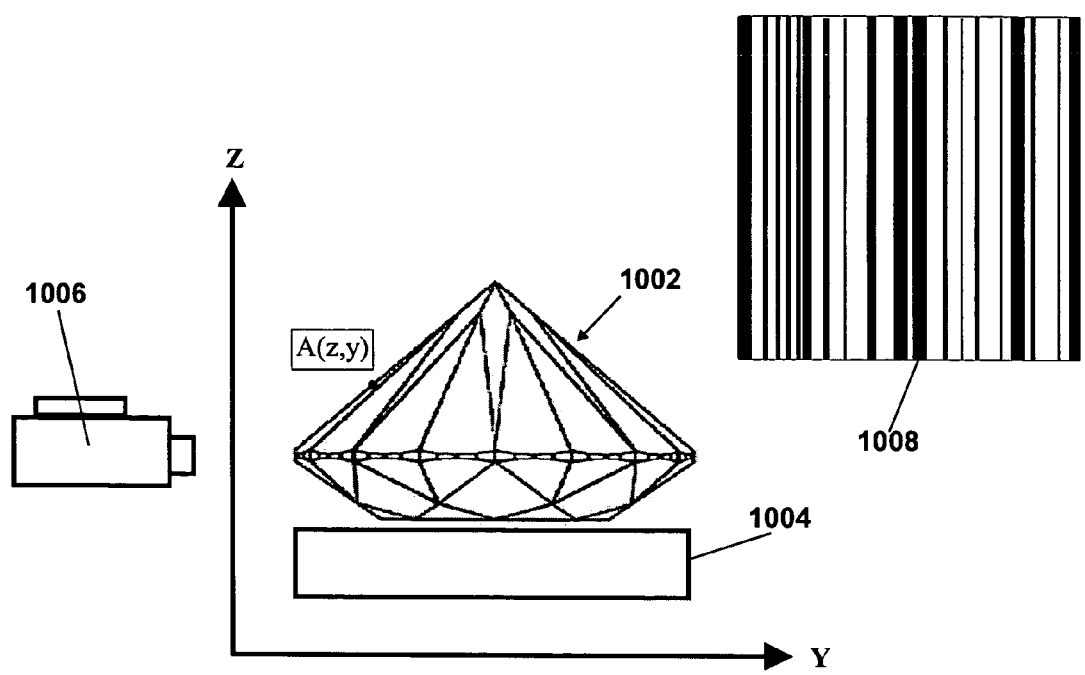
FIGS. 10A and 10B illustrate an alternative arrangement for locating a facet of a diamond according to the present invention.
Figure 10B:
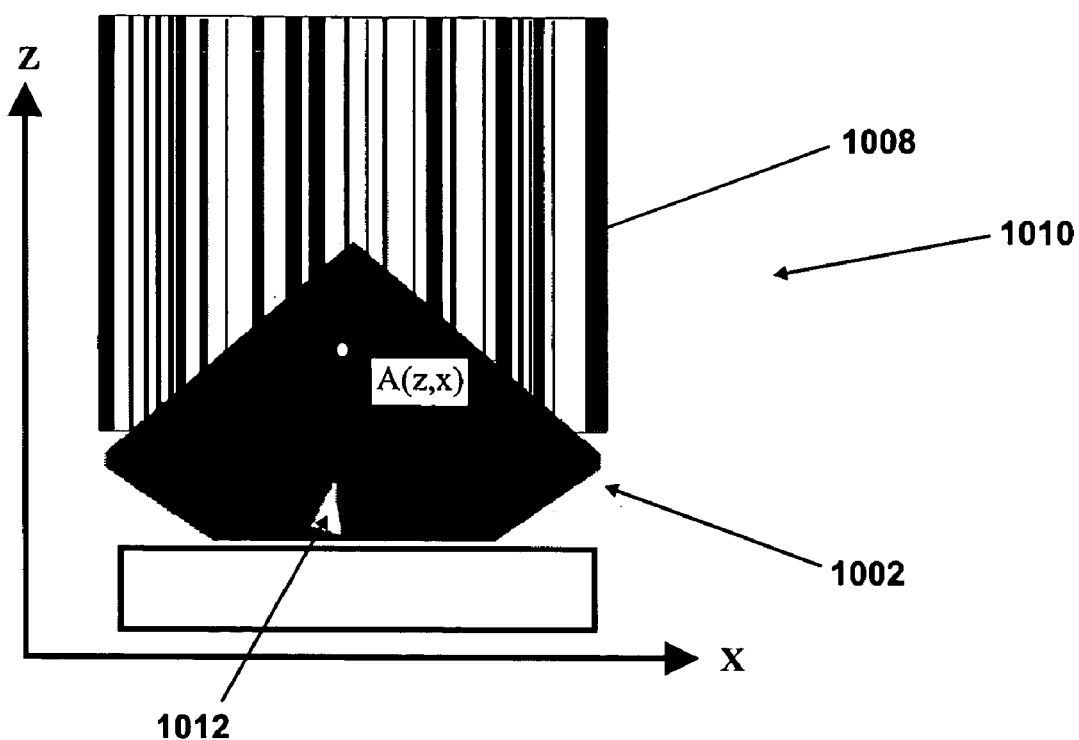

A further embodiment of the present invention is shown in FIGS. 10A and 10B, which has the benefit of greater simplicity than the previously described embodiments. In this further embodiment, the lighting source includes means for generating light having a plurality of colours or shades. Coloured light passing through and reflecting from the diamond 1002 is fragmented by the facet structure of the diamond such that discontinuities in the fragmented image may be analysed to identify the edges of a facet of the diamond.

In the embodiment of FIGS. 10A and 10B, the colours or shades of light are generated by placing a screen 1008 including a plurality of coloured or shaded bands behind the diamond. The arrangement is lit using a broad spectrum lighting source such as a white light source. The light source may be a dedicated broad spectrum light emitter (not shown), or ambient lighting may be used if suitable. The diamond 1002 is then rotated on the turntable 1004 such that the facet to be measured faces the camera 1006. An image 1010 is then captured, and can be analysed for discontinuities in the fragmented colour patterns, e.g. bright region 1012, in order to identify the facet location and dimensions.

CONCLUSION

A method and apparatus according to the present invention may be employed to locate the facets of a diamond with greater accuracy than is possible using the prior art methods previously described. Accordingly, the problems associated with using a model of the diamond obtained by prior art methods, including errors in determining the junctions of facet edges, may be mitigated. Furthermore, the dependence upon experts with specialised skills, experience and knowledge for assessing properties of the diamond such as symmetry may be reduced.

Furthermore, it is envisaged that the present invention will be useful for diamond cut quality grading through the constructions of three-dimensional models that may be used with ray tracing software to predict the basic light responses, such as brilliancy, contrast and dispersiveness.

The present invention is not limited in scope to the described embodiment or embodiments but rather the scope of the present invention is broader so as to encompass, for example, other forms of the apparatus, other methods of orienting a diamond with respect to the image capture means, and other means of selectively lighting the diamond.

I claim:

1. A method of measuring a physical characteristic relating to location and/or dimensions of a facet of a diamond, the method comprising the steps of:

illuminating the diamond to visually distinguish said facet from adjacent facets when viewed from a predetermined viewing location;

capturing an image of the diamond as viewed from said viewing location;

determining positional data of at least one point located on an edge of said facet by analyzing the image, wherein said analyzing comprises identifying a discontinuity, internal to a corresponding silhouette boundary of the captured image, in the properties of light transmitted from the diamond to the viewing location, and constructing a data set representing location and/or dimensions of the facet using said positional data, wherein said data set may be used in computer analysis to provide a user with information relating to a physical characteristic of the diamond, such as symmetry, and/or in computer modeling of light response characteristics of the diamond to provide the user with an assessment of diamond cut quality.

2. The method of claim 1 wherein said predetermined viewing location is substantially positioned in a plane oriented perpendicular to a surface of said facet and the direction of viewing from said predetermined location is towards the diamond along a line substantially normal to an axis thereof.

3. The method of claim 1 wherein the step of illuminating comprises illuminating the diamond using a controlled lighting source.

4. The method of claim 3 wherein said controlled lighting source comprises an array of discrete light emitters, and the step of illuminating the diamond includes activating or deactivating one or more emitters of the array.

5. The method of claim 1 wherein the step of illuminating includes illuminating the diamond using a source of light having a plurality of colours and/or shades.

6. The method of claim 5 wherein the step of illuminating comprises illuminating a screen having a plurality of bands of varying or discontinuous colour or shade, said screen being placed substantially behind the diamond relative to the viewing location, such that said facet is visually distinguished by means of discontinuities in colour or shade of light emitted from a surface of said facet after being transmitted from said screen through the diamond.

7. The method of claim 1 wherein the step of illuminating comprises illuminating the diamond using one or more light emitters located relative to the viewing location such that the facet is visually distinguished by light reflected by the facet.

8. The method of claim 1 wherein the step of illuminating comprises illuminating the diamond using one or more light emitters located relative to the viewing location, such that the facet is visually distinguished by light transmitted through the diamond and emitted from said facet.

9. The method of claim 1 wherein the step of capturing an image includes capturing a digital image, and the step of determining positional data includes analyzing the digital image using a computer.

10. The method of claim 1 wherein said discontinuity is between adjacent brighter and darker regions of said image.

11. The method of claim 10 wherein said brighter region results from light generated by a source of illumination and reflected from a surface of said facet towards the viewing location.

12. The method of claim 10 wherein said brighter region results from light generated by a source of illumination and transmitted through the diamond and emitted from a surface of said facet.

13. The method of claim 1 wherein said discontinuity is between adjacent regions of differing colour or shade resulting from light generated by a source having a plurality of colours or shades, said light being transmitted through the diamond and emitted from respective surfaces of said adjacent facets.

14. The method of claim 13 wherein said source comprises a light emitter and a screen having a plurality of bands of varying or discontinuous colour or shade.

15. The method of claim 1 wherein the step of determining positional data comprises determining an unknown coordinate of the at least one point located on said edge by identifying a point on the edge corresponding to at least one known coordinate of said point.

16. The method of claim 1 wherein the step of determining positional data comprises determining at least one unknown coordinate by identifying a point on a line corresponding to at least one known coordinate of said point at which there is a discontinuity in the properties of the light transmitted from the diamond to the viewing location.

17. An apparatus for measuring a physical characteristic relating to location and/or dimensions of a facet of a diamond, the apparatus comprising:

a support for the diamond within the apparatus;

at least one camera positionable at a predetermined location for capturing an image of the diamond;

a light source for illuminating the diamond to visually distinguish said facet from adjacent facets when viewed from the location of the camera; and a processor for analyzing said image to determine positional data of at least one point located on an edge of said facet by analyzing the image, wherein said analyzing comprises identifying a discontinuity, internal to a corresponding silhouette boundary of the captured image, in the properties of light transmitted from the diamond to the viewing location.

18. The apparatus of claim 17 wherein said camera is located at a fixed position relative to the support, and the support is operable to orient the diamond relative to the camera.

19. The apparatus of claim 18 wherein said support comprises a turntable operable to rotate the diamond.

20. The apparatus of claim 17 wherein the light source comprises a controlled light source.

21. The apparatus of claim 20 wherein said controlled light source comprises an array of discrete light emitters, each of which may be independently activated or deactivated.

22. The apparatus of claim 17 wherein said light source comprises a plurality of colours or shades.

23. The apparatus of claim 22 wherein said light source comprises at least one light emitter and a screen having a plurality of bands of varying or discontinuous colour or shade, said screen being located substantially behind the diamond relative to the location of the camera.

24. The apparatus of claim 17 wherein the camera comprises a digital camera and the processor comprises a computer configured to receive a digital image and programmed to analyze said image to determine the location of at least one point located on an edge of said facet.

25. The apparatus of claim 17 wherein the processor is configured to determine an unknown coordinate of at least one point located on said edge by identifying a point on the edge corresponding to at least one known coordinate of said point.

26. The apparatus of claim 17 wherein the processor is configured to determine at least one unknown coordinate by identifying a point on a line corresponding to at least one known coordinate of said point at which there is a discontinuity in the image.

27. A method of obtaining data for the construction of a three dimensional model of a diamond comprising the steps of:
- illuminating the diamond to visually distinguish each facet of said diamond from adjacent facets when viewed from a predetermined viewing location;
- capturing images of each of the visually distinguished facets of the diamond as viewed from said viewing location;
- analyzing said images to determine positional data of a plurality of points located on the edges of said facets, wherein said analyzing comprises identifying discontinuities, internal to corresponding silhouette boundaries of the captured images, in the properties of light transmitted from the diamond to the viewing location; and
- constructing a data set comprising the locations of the edges of all of said facets of the diamond using said positional data,
- wherein said data set may be used in computer analysis to provide a user with information relating to a physical characteristic of the diamond such as symmetry, and/or in computer modeling of light response characteristics of the diamond to provide the user with an assessment of diamond cut quality.

28. The method of claim 27 further comprising the steps of:
- constructing an initial approximate model of the diamond;
- using the approximate model to determine a plurality of illumination configurations for use in the illuminating step to visually distinguish each facet of said diamond from adjacent facets when viewed from the predetermined viewing location, and
- wherein the step of analyzing comprises determining a plurality of points located on the edges of said facets to determine locations of the edges of all of said facets of the diamond, and using said determined locations of the edges to refine said approximate model.

29. The method of claim 28 wherein the step of constructing an initial approximate model comprises constructing a model of the diamond using a silhouette grading method.

30. A method of constructing a three dimensional model of a diamond comprising the steps of:
- constructing a data set comprising an initial approximate model of the diamond using a silhouette grading method;
- using the approximate model to determine a plurality of illumination configurations whereby each facet of the diamond is visually distinguishable from adjacent facets when viewed from a corresponding predetermined viewing location;
- successively illuminating the diamond in accordance with each of said illumination configurations and capturing images of each of the visually distinguished facets of the diamond as viewed from said viewing locations;
- analyzing said images to determine positional data of a plurality of points located on the edges of said facets, wherein said analyzing comprises identifying discontinuities, internal to corresponding silhouette boundaries of the captured images, in the properties of light transmitted from the diamond to the viewing location; and
- constructing a data set comprising a three dimensional model of the diamond using said positional data, wherein said three dimensional model has improved accuracy as compared with the initial approximate model,
- wherein said data set may be used in computer analysis to provide a user with information relating to a physical characteristic of the diamond, such as symmetry, and/or in computer modeling of light response characteristics of the diamond to provide the user with an assessment of diamond cut quality.

* * * * *